(12) United States Patent
Mansfield et al.

(10) Patent No.: US 9,324,468 B2
(45) Date of Patent: Apr. 26, 2016

(54) MULTILEAF COLLIMATORS WITH TRANSVERSE MOTION

(75) Inventors: Stanley Mansfield, Sunnyvale, CA (US); Steven W. Prince, San Francisco, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1234 days.

(21) Appl. No.: 12/861,373

(22) Filed: Aug. 23, 2010

(65) Prior Publication Data

US 2012/0043481 A1 Feb. 23, 2012

(51) Int. Cl.
*G21K 5/04* (2006.01)
*G21K 1/04* (2006.01)
*A61N 5/10* (2006.01)

(52) U.S. Cl.
CPC .............. *G21K 1/046* (2013.01); *A61N 5/1045* (2013.01)

(58) Field of Classification Search
USPC ............ 250/396 R, 398, 492.1, 492.3, 505.1, 250/515.1, 517.1; 378/145, 147, 148, 149, 378/150, 151, 152, 153
See application file for complete search history.

(56) References Cited

U.S. PATENT DOCUMENTS

| | | | |
|---|---|---|---|
| 4,489,426 A * | 12/1984 | Grass et al. | 378/150 |
| 5,591,983 A | 1/1997 | Yao | |
| 6,144,875 A | 11/2000 | Schweikard et al. | |
| 6,977,987 B2 | 12/2005 | Yamashita et al. | |
| 7,085,347 B2 | 8/2006 | Mihara et al. | |
| 7,188,999 B2 | 3/2007 | Mihara et al. | |
| 7,221,733 B1 | 5/2007 | Takai et al. | |
| 7,239,684 B2 | 7/2007 | Hara et al. | |
| 2002/0101959 A1 | 8/2002 | Kato | |
| 2004/0079899 A1 * | 4/2004 | Ma | 250/492.3 |
| 2004/0168536 A1 | 9/2004 | Bellouard | |
| 2007/0176126 A1 * | 8/2007 | Hashimoto | G21K 1/04 250/495.1 |
| 2009/0041200 A1 * | 2/2009 | Lu et al. | 378/152 |
| 2009/0207975 A1 | 8/2009 | Bourne | |
| 2010/0189220 A1 * | 7/2010 | Flynn et al. | 378/65 |
| 2010/0252754 A1 * | 10/2010 | Brown et al. | 250/492.1 |

FOREIGN PATENT DOCUMENTS

| | | |
|---|---|---|
| DE | 19905823 C1 | 6/2000 |
| EP | 0314214 A2 | 5/1989 |
| EP | 0562644 A1 | 9/1993 |
| JP | H07255716 A | 10/1995 |
| WO | 2008/076035 A1 | 6/2008 |
| WO | 2009/056151 A1 | 5/2009 |

OTHER PUBLICATIONS

PCT, International Search Report and Written Opinion in International Application No. PCT/US2011/048203, Mar. 23, 2012, 9 pages.

(Continued)

*Primary Examiner* — Nicole Ippolito
(74) *Attorney, Agent, or Firm* — Houst Consulting

(57) ABSTRACT

A collimation assembly includes a multileaf collimator and motion assembly. The multileaf collimator includes a support body and a plurality of pairs of beam blocking leaves supported by the support body. The beam blocking leaves are longitudinally movable in a first direction. The motion assembly includes an actuator and a guide assembly operable to move the support body and thereby allowing the plurality of pairs of beam blocking leaves to move in a second direction generally transverse to the first direction.

24 Claims, 11 Drawing Sheets

(56) References Cited

OTHER PUBLICATIONS

Hirai et al. "State-of-the-Art Medical Treatment Machine MHI-TM2000," Mitsubishi Heavy Industries Technical Review, Mar. 2009, vol. 46 No. 1, pp. 29-32.

EPO, Extended European Search Report in European Application No. 11820404.9, Feb. 5, 2015, 5 pages.

State Intellectual Property Office of China, Search Report and Office Action in Chinese Application No. 201180042834.3, Mar. 25, 2015, 13 pages.

* cited by examiner

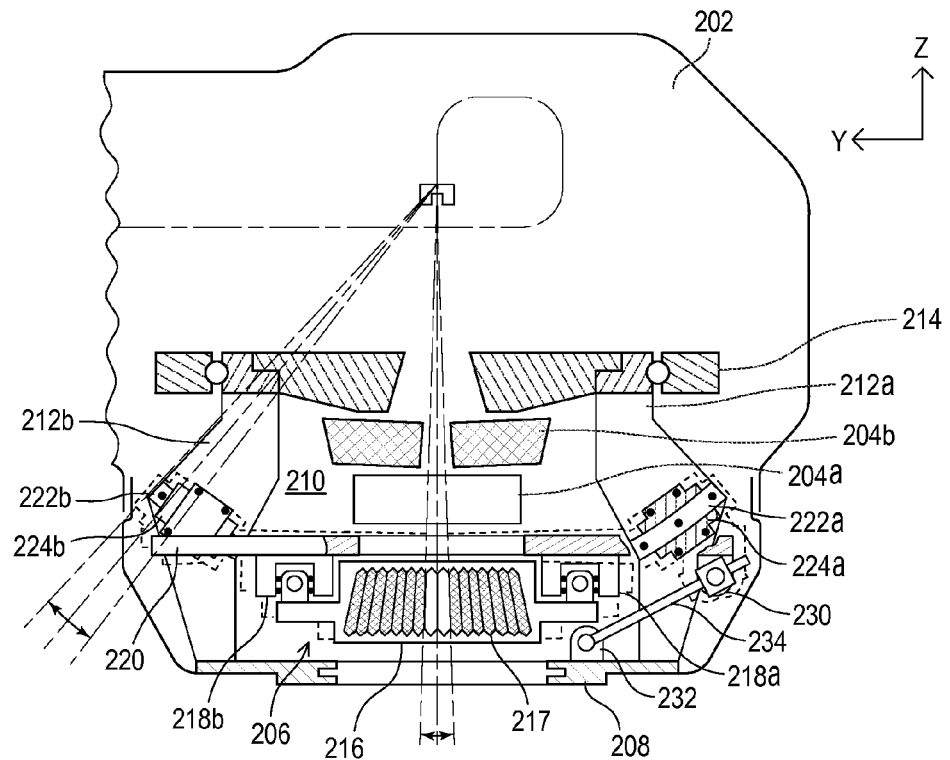
FIG. 2
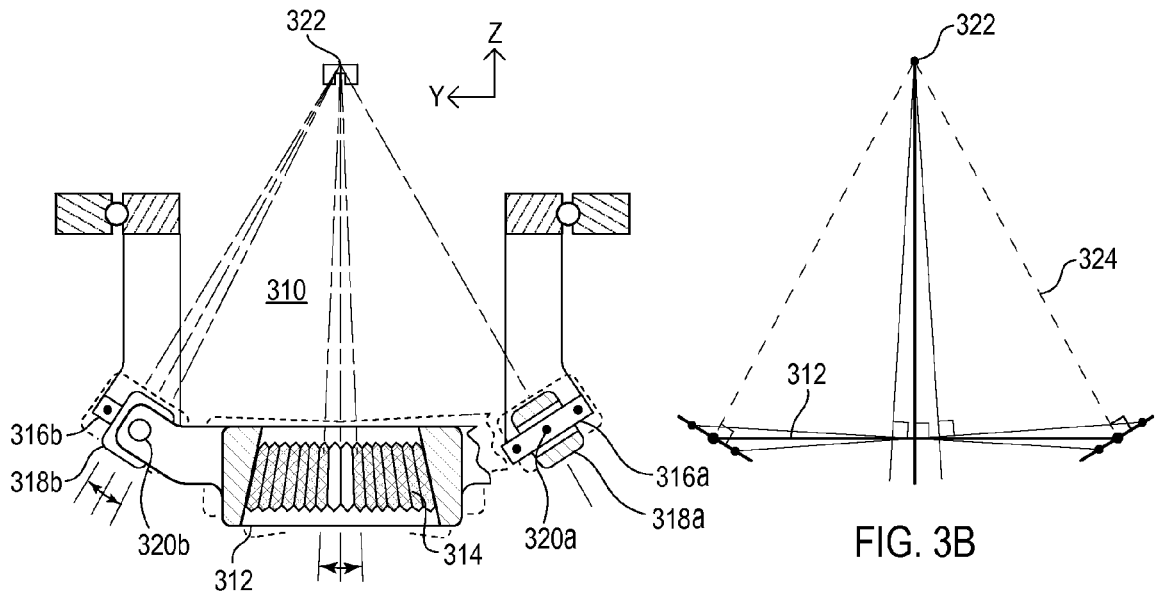
FIG. 3A
FIG. 3B

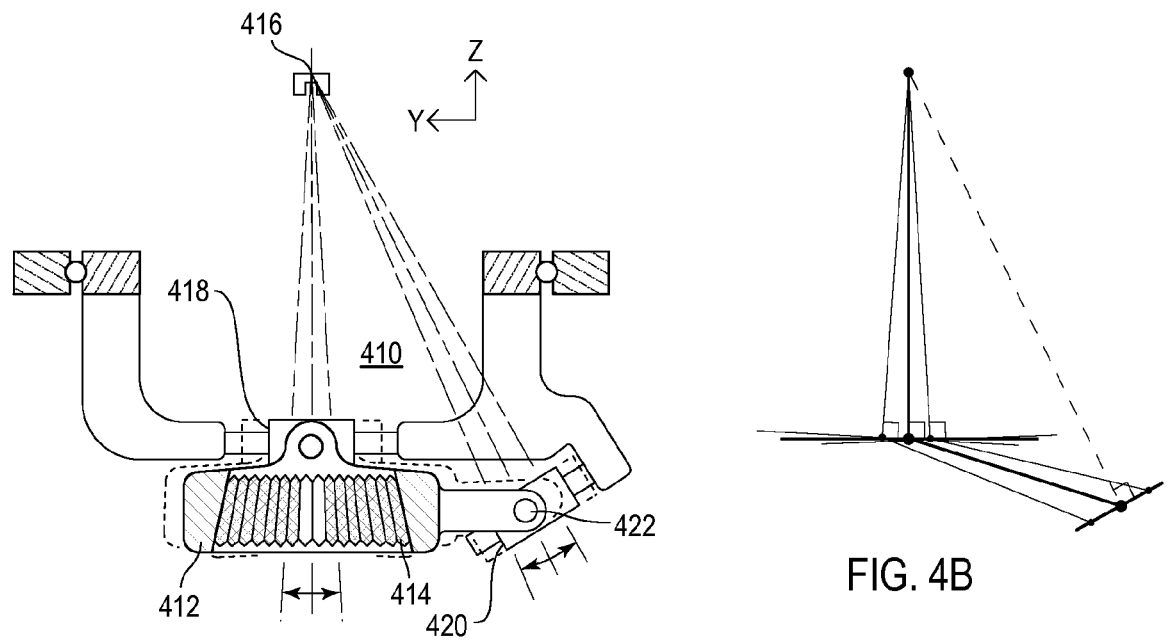
FIG. 4A
FIG. 4B
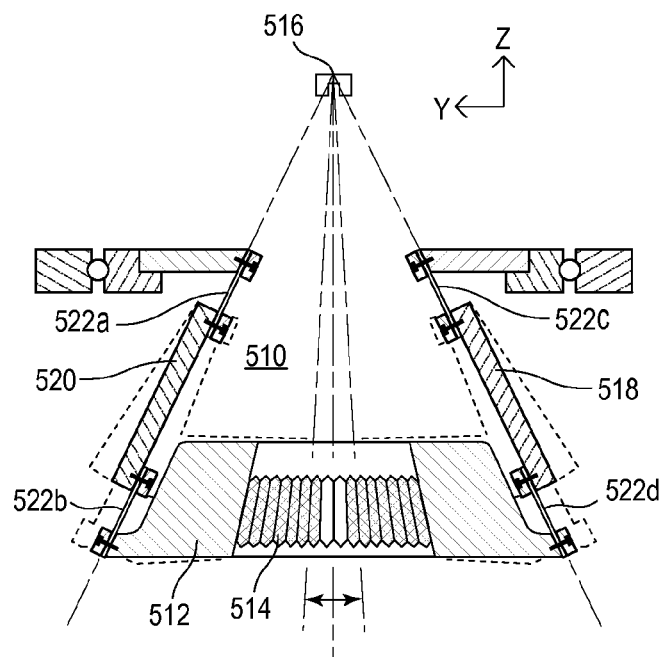
FIG. 5A

MULTILEAF COLLIMATORS WITH TRANSVERSE MOTION

BACKGROUND

This invention relates generally to radiation apparatuses and methods, and in particular to multileaf collimators and methods of adjusting radiation beams useful in radiotherapy of diseases and other applications.

Radiation therapy is in common use in treating patients having tumors. One issue in radiation therapy is the movement of patient's internal organs caused by breathing. The internal organs' movement is significant enough that delivery of treatment dose to a fixed location may risk overdose to healthy organs and/or underdose to tumors. Conventional techniques include gating the radiation beam so that the beam is on only during stable and repeatable portions of the breathing cycle. Gating the beam on and off involves not treating during a large portion of the breathing cycle, therefore significantly increasing treatment time. This is compounded by the modulation factors of intensity-modulated radiation therapy (IMRT) that also increase the beam-off time. In arc therapy gating requires difficult starting and stopping the motion of a massive gantry, so gating is usually not implemented.

Another conventional technique includes moving the patient on a tracking couch so that the tumor remains stationary relative to a treatment field. Moving a patient using a tracking couch during treatment is generally deemed undesirable. Although the required patient acceleration may be slight, moving the patient introduces uncertainties in the position of soft tissues particularly if the patient reacts to the motion by tensing. The variations of motor noise and vibration may be disconcerting to the patient.

SUMMARY

A collimation assembly including a multileaf collimator and a motion assembly is provided. The multileaf collimator comprises a support body and a plurality of pairs of beam blocking leaves supported by the support body. The beam blocking leaves are longitudinally movable in a first direction. The motion assembly includes an actuator and a guide assembly operable to move the support body and thereby allowing the plurality of pairs of beam blocking leaves to move in a second direction generally transverse to the first direction.

A radiation apparatus including a radiation source and a collimation assembly is provided. The collimation assembly may include a multileaf collimator, a motion assembly, and other fixed and movable beam limiting devices. The multileaf collimator includes a support body and a plurality of pairs of beam blocking leaves supported by the support body in one or more planes, and the leaves of each pair are longitudinally movable relative each other. The motion assembly includes an actuator and a guide assembly operable to move the support body thereby allowing the one or more planes of the beam blocking leaves to rotate about the radiation source.

In a radiation method, the shape and motion of a target in a subject is determined. A radiation beam is provided from a source to the target. A treatment field substantially conforming to the shape of the target is defined using a multileaf collimator assembly comprising a support body and a plurality of beam blocking leaves supported by the support body. The defined treatment field is moved by moving the support body with the motion of the target.

BRIEF DESCRIPTION OF THE DRAWINGS

These and various other features and advantages will become better understood upon reading of the following detailed description in conjunction with the accompanying drawings and the appended claims provided below, where:

FIG. 2 illustrates a cross-section of a portion of a radiation system that includes a collimation assembly in accordance with another embodiment of the invention;

FIG. 3A illustrates a cross-section of a collimation assembly in accordance with another embodiment of the invention;

FIG. 3B is a schematic geometry diagram showing transverse motions of the collimation assembly illustrated in FIG. 3A;

FIG. 4A illustrates a cross-section of some elements of a collimation assembly in accordance with another embodiment of the invention;

FIG. 4B is a schematic geometry diagram showing transverse motions of the elements of the collimation assembly illustrated in FIG. 4A;

FIG. 5A illustrates a cross-section of an exemplary collimation assembly in accordance with some embodiments of the invention;

DETAILED DESCRIPTION

Various embodiments of multileaf collimator assemblies are described. It is to be understood that the invention is not limited to the particular embodiments described as such which may, of course, vary. An aspect described in conjunction with a particular embodiment is not necessarily limited to that embodiment and may be practiced in any other embodiments. For instance, while various embodiments are described in connection with X-ray radiotherapy machines, it will be appreciated that the invention can also be practiced in other radiation apparatuses and modalities. It is also to be understood that the terminology used herein is for the purpose of describing particular embodiments only, and is not intended to be limiting since the scope of the invention will be defined by the appended claims, along with the full scope of equivalents to which such claims are entitled. In addition, various embodiments are described with reference to the figures. It should be noted that the figures are intended to facilitate the description of specific embodiments and they are not intended as an exhaustive description or as a limitation on the scope of the invention.

Various relative terms such as "upper," "above," "top," "over," "on," "below," "under," "bottom," "higher," "lower" or similar terms may be used herein for convenience in describing relative positions, directions, or spatial relationships in conjunction with the drawings. The use of the relative terms should not be construed as to imply a necessary positioning, orientation, or direction of the structures or portions thereof in manufacturing or use, and to limit the scope of the invention. As used in the description and appended claims, the singular forms of "a," "an," and "the" include plural references unless the context clearly dictates otherwise. For example, reference to "a direction" includes the opposite direction of the direction and/or a plurality of directions that are parallel to the direction. A direction includes both linear and arc trajectories. As used herein the term "support body" may include a single support body member or a support body assembly comprised of a plurality of body members. The term "plane" as used in the plane of beam blocking leaves include both planar and curved or spherical plane.

Figure 1:
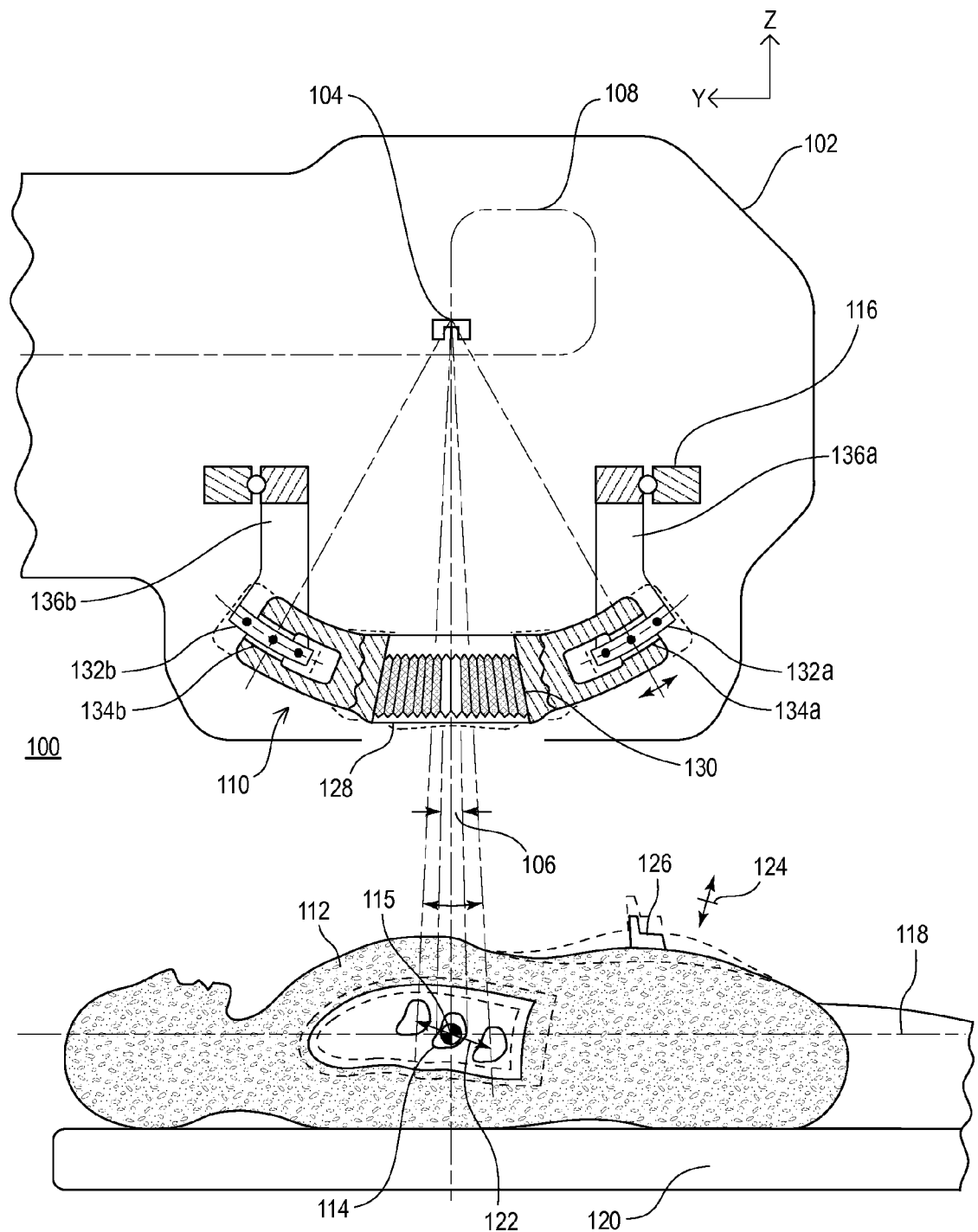
FIG. 1 illustrates a cross-section of a portion of a radiation system and a patient in accordance with one embodiment of the invention. The cross-section shown is perpendicular to the leaf motion direction. Some elements of the collimation assembly are omitted for clarity.

FIG. 1 is a simplified cross-sectional illustration of a portion of a radiation system 100 that includes an exemplary collimation assembly 110 in accordance with some embodiments of the invention. The system 100 includes a treatment head 102 that houses various components configured to produce, shape or monitor a treatment beam. A radiation source 104 may be configured to produce treatment beams 106 such as beams of photons, protons, electrons, or other types of particles. For example, in an X-ray radiotherapy system the radiation source 104 may include a target which can produce X-ray radiation when impinged by energetic electron beams 108. A collimation assembly 110 may be disposed between the radiation source 104 and a patient 112. The collimation assembly 110 may include a multileaf collimator operable to selectively block the radiation beams from the radiation source. The multileaf collimator may comprise a plurality of beam blocking leaves 130 operable in pairs to form apertures to adjust the shape and/or modulate the intensity of the beam 106 projected to a tumor 114 in the patient. The collimation assembly 110 may also include other collimation elements such as primary and secondary fixed collimators, and movable collimation jaws etc. For clarity and to focus on description of the invention these additional collimation elements are not shown FIG. 1. Because the illustration is a cross-section, some of the elements are not shown. The elements not shown may be substantially symmetrical about the cross-section plane. The collimation assembly 110 may rotate e.g. on a bearing 116 about an axis through the source 104 and the isocenter 115. The treatment head 102 may rotate about an axis through the isocenter 115 such as a horizontal axis 118 through a tumor in the patient. The patient 112 may be supported on a treatment couch top 120 which may be cantilevered from the floor. Thus in some embodiments, the radiation system 100 can deliver a treatment beam to a tumor in the patient from multiple angles, and the shape and/or intensity of the beam can be dynamically adjusted by the collimation assembly 110 as the beam angle is swept or stepped around the target.

Patient breathing produces movement of organs in the torso in various directions. A tumor usually moves in a manner that is fairly repeatable 122. The tumor motion 122 can be measured by imaging or sensing implanted seeds, and can be predicted by correlation to the motion of the patient's abdomen 124. Movement of the abdomen 124 can be relatively easily measured by tracking external devices such as a respiratory gating block 126.

The collimation assembly 110 may include a support body 128 and a plurality of beam blocking leaves 130. The plurality of beam blocking leaves 130 may be arranged in two arrays (FIG. 1 shows a cross-section through one of two arrays), forming a plurality of pairs of opposing leaves. The leaves 130 may be in various configurations in cross section such as rectangle or trapezoid etc. By way of example, the leaves 130 may have a cross section that is approximately trapezoidal in shape with leaf sides substantially focused on the source. The leaf sides may have smaller features not shown such as steps, waves, or slight tilt to reduce the radiation passing through leaf gaps. The size of the cross sections of the leaves 130 may be same or variable. For example, the plurality of beam blocking leaves 130 may include a middle section of narrower leaves to provide higher leaf definition and an outer section of wider leaves where high definition may not be required. The beam blocking leaves 130 may be arranged in one level. In some embodiments, the beam blocking leaves 130 may be arranged in two or more levels to improve various leakage effects and MLC definition. U.S. application Ser. No. 12/861,268 entitled "Multi Level Multileaf Collimators" filed concurrently with this application discloses various embodiments of multi level MLCs, the disclosure of which is incorporated herein by reference. Each of the beam blocking leaves 130 can be independently moved (e.g. in the x-direction) by a drive motor (not shown). The drive motors can be secured to the support body or assembly of bodies 128 and coupled to a computer and motion control. In operation the drive motors receive signals from the computer and motion control and move to position individual leaves 130 relative to the beam direction based on a treatment plan. The positioning of a leaf operates to block or adjust the radiation beam passing through the volume occupied by the leaf. The combined positioning of all leaves at any time in the execution of the treatment plan may define one or more apertures through which the unblocked radiation beam passes, and the aperture(s) may define the shape of the radiation beam directed to a treatment field at the isocenter. The combined effect of the blocking and open apertures in the treatment plan creates the desired three-dimensional radiation dose distribution within the patient.

The support body 128 may include a frame, box or carriage etc. supporting the beam blocking leaves 130. In some embodiments, all the beam blocking leaves 130 may be supported by a box or carriage, which may be driven by a mechanism in the same direction as the leaf travel direction (e.g. in the x direction). In some embodiments, each array of the beam blocking leaves may be supported by a separate carriage, and each carriage may be driven by a mechanism in the same direction as the leaf travel direction. Various arrangements and types of guide rails and powered actuators can be used to support and move MLC boxes or carriages. The use of one or more movable carriages may provide advantages in that individual leaves and their travel can be shorter, and therefore have better tolerance control, less cost, less weight, and can fit within a smaller cover or similar structures. Combined speed of leaves and carriages can be a treatment planning advantage. In some embodiments, the collimation assembly 110 does not require a movable carriage and it will be appreciated that this invention can apply to collimation assemblies with or without movable carriages.

The support body 128 may be driven by an actuating mechanism such as a powered actuating mechanism as will be described in greater detail below. As a result, the beam blocking leaves 130 supported by the support body 128 may be provided with one or more motion degrees of freedom in addition to the travel of individual leaves. The additional motion degrees of freedom of the beam blocking leaves may be in a direction different from and/or same as the individual leaf travel direction. In various embodiments, these degrees of freedom may be arranged at many different levels of structural hierarchy from the support body up to and including the collimator bearing. Therefore, in some embodiments the transverse motion of the beam blocking leaves may be provided by moving the entire collimation assembly comprising the support body. In some embodiments the transverse motion may be provided by moving the collimator bearings relative to the gantry. If the collimation assembly 110 optionally includes movable carriages as described above, the motion of the support body 128 may also provide the carriages additional motion degrees of freedom. By way of example, the collimation assembly 110 may be constructed such that the support body 128 may be moved to allow the beam blocking leaves 130 to move in a direction (e.g. the y direction) generally transverse to the individual leaf travel direction (e.g. the x-direction). Providing a collimation assembly 110 with a transverse motion can be advantageous in tracking tumors which move in a direction that does not match the MLC leaf travel direction. For any tumor movement that is transverse to the MLC leaf travel direction, the computer and control system may respond by moving the support body e.g. in the y direction rather than moving individual MLC leaves in the x direction. This can avoid zipper-like movement of individual MLC leaves as in conventional systems, allow simplification of the treatment planning and system control, and improve the accuracy of shaping the treatment field edge regions in the locations most subject to the transverse movement.

The support body 128 may also be moved in a direction generally parallel to the leaf travel direction (e.g. the x direction). Providing the support body 128 with a motion degree of freedom in the x direction can be advantageous in that it increases the travel and/or speed of the beam blocking leaves without addition of movable carriage or carriages. This is possible because such x-direction motion would rotate the entire collimation assembly approximately about the radiation source. In some embodiments, the support body 128 may be moved in both the x and y directions.

The support body 128 may be moved in a linear trajectory for a small motion. In some embodiments the support body 128 may be moved in perfect arc trajectory approximately centered at the radiation source 104, as shown in FIG. 1. In other embodiments, the trajectory may approximate a perfect arc approximately centered at the radiation source. The rotation of the support body and thus the projected treatment field may result in a slight "keystone" distortion of the projected MLC square grid into a trapezoid. The distortion would be negligible for the few centimeters of projected offset. As can be seen the axis of rotation of the leaf pair is at an angle with respect to the axis of the beam line 106. In the illustrated embodiment, this axis is positioned roughly such that it intersects the beam line 106 at an approximately 90 degree angle to beam line 106, although in alternative embodiments the position of the axis and its angle relative to the beam line 106 axis can be other than as shown.

Various mechanisms can be used to move and guide the motion of the support body 128. For example, a powered actuating mechanism including a ball screw driven by an electric motor may be used to move the support body 128. The motion of the support body 128 can be guided by guides 132a, 132b and bearings 134a, 134b or other suitable components. The guides 132 and bearings 134 can be linear or curved guides and bearings. Depending on the stiffness of the guide components chosen, different number of guide/bearing structures may be used in different locations or cross sections to provide rigid support. By way of example, in some embodiments shown in FIG. 1, the guide components may include curved guide rails 132 of various curvature or shape to constrain the motion of the support body 128. The curved guide rails of specific shapes can be combined with curved bushings, recirculating bearing blocks, or cam followers etc. The guide rails 132 may be on a separate support structure 136a, 136b as shown in FIG. 1. Alternatively, the curved guide rails 132 can be on the support body 128 and move with the support body.

FIG. 2 schematically illustrates a treatment head 202 including an exemplary collimation assembly 210 in accordance with some embodiments. The collimation assembly 210 may include other beam limiting components such as pairs of jaw assemblies motorized in the x-direction 204a and the y-direction 204b above and/or below a multileaf collimator 206. Below the multileaf collimator 206 can be an accessory mount 208. Rigid structure 212a, 212b may support the heavy components from the collimator bearing 214 with additional rigid structures not visible in this cross-section, for example, two more structures not shown. The collimation assembly 210 may include a pair of MLC boxes 216 each supporting an array of beam blocking leaves 217 as described above. The boxes 216 may be on carriages which may move on linear bearings 218a, 218b in the leaf travel direction (e.g. in the x direction). The linear bearings 218a, 218b may be mounted to a base plate 220 which may be supported by a guide system including guide rails 222a, 222b and bearings 224a, 224b. FIG. 2 shows curved guide rails 222a and 222b mounted on the rigid support structure 212a, 212b. In operation, the collimation assembly 210 including the base plate 220, both MLC boxes 216, and the beam blocking leaves 217 supported by the MLC boxes can be moved in a direction e.g. generally transverse to the MLC leaf travel direction. The jaw assemblies 204a and 204b may be supported by rigid collimator structure such as the rotating race of collimator bearing 214, and/or by support structure 212. Alternatively, jaw assemblies 204 could be supported by the base plate 220. In the former case, they may adjust to small transverse motions as needed using their own drive systems. In the latter case, they would move with the small transverse motions as part of the same moving body.

The actuating mechanism 234 may include a linear actuator connecting the base plate assembly 220 to any part of the rigid collimator structure such as accessory mount 208 through pivot points 230, 232. Many types of linear actuators can be used. By way of example, an actuator may include an integrated linear motion stage with a zero-backlash ballscrew and ballnut drive powered by a brushless DC electric motor with redundant feedback mechanisms. The actuating mechanism should be sufficiently powerful to move against gravity and sufficiently stiff to minimize gravity-induced motion due to stiffness and backlash on the degree of freedom that it controls. One of the advantages of the collimation assembly of the invention is that it can compensate for the inevitable gravity induced deflection of the gantry structure that supports the heavy treatment head and for any mechanical misalignment in the gantry and collimator rotational axes. By utilizing small motions of the MLC transverse motion in concert with leaf or carriage motion, the MLC can thus compensate for these effects to reduce or eliminate variation of the treatment isocenter due to deflection. In some embodiments, the actuating mechanism may include dual position feedback systems so that position feedback would not be subject to a single point of failure. For example, in some embodiments a rotary resolver may be coupled to a motor shaft and a linear resolver coupled to either the actuator motion or the MLC motion. The linear resolver can alternatively be a rotary resolver driven by a linear device such as a rack or a belt with suitable zero-backlash provision such as an anti-backlash gear or anti-backlash belt tooth profile. U.S. application Ser. No. 12/568,621 filed Dec. 18, 2009 discloses various methods and systems for positioning motion axes, the disclosure of which is incorporated herein by reference.

FIG. 3A illustrates an alternative construction of a collimation assembly 310 in accordance with some embodiments of the invention. For clarity some beam limiting elements or other devices typically contained in a collimation assembly are omitted in FIG. 3A. The collimation assembly 310 illustrated in FIG. 3A is similar to the collimation assembly 110 illustrated in FIG. 1 in many aspects, and includes a support body 312 and a plurality of beam blocking leaves 314 supported by the support body 312. In comparison, the collimation assembly 310 illustrated in FIG. 3A includes linear guide components such as linear guide rails 316a and 316b and linear bearings 318a and 318b whereas the collimation assembly 110 illustrated in FIG. 1 includes curved guide components. Linear guide components are more commonly available and more economical. Due to structural over-constraint, the connection of the support body 312 to the linear guide components 318a and 318b should accommodate a small amount of rotation about the x axis. The rotation accommodation is shown as pivot joints 320a, 320b in FIG. 3A. Alternatively, the structural over-constraint can be accommodated by a flexure, an opposed pair of cam followers, or linear components that allow for sufficient misalignment. FIG. 3B is a geometry diagram simplifying the MLC support body 312 and the virtual focus 322 of the MLC. The darker lines indicate a center position of the support body 312, the fainter lines indicate extreme positions, and the dark dots indicate the motion in the guides. FIG. 3B shows the linear movement constrained by the linear guide components, but the angle of the linear guides insures that a perpendicular line 324 through the center position still passes approximately through the radiation source 322. The MLC leaf plane and the treatment field shaped by the MLC move approximately in an arc trajectory approximately centered on the source 322.

FIG. 4A illustrates another alternative construction of a collimation assembly 410 in accordance with some embodiments of the invention. The collimation assembly 410 includes a support body 412 and a plurality of beam blocking leaves 414 substantially focused on a source 416. In comparison with the collimation assembly 310 illustrated in FIG. 3A, the collimation assembly 410 illustrated in FIG. 4A also includes linear guides 418, 420, but without the symmetric arrangement as shown in FIG. 3A. The linear guides 418, 420 can be repeated at two or more locations (not shown in this cross-section) to insure rigid support. The linear guides 418, 420 are preferably located off the collimator axis to avoid obscuring the treatment beam. Similar to the construction of the collimation assembly 310 illustrated in FIG. 3A, the connection of the support body 412 to the linear guides 418, 420 should accommodate a small amount of rotation about the x axis due to structural over-constraint. The rotation accommodation can be pivot joints, flexures, or other mechanisms 422. The geometric principle shown in FIG. 4B is related to the principle of a sine bar. FIG. 3B and FIG. 4B can be geometric special cases of the generic case of a body with two points moving on linear guides. One of the advantages of the collimation assembly 410 illustrated in FIG. 4A is that the central horizontal linear guide 418 can support the majority of the load and the angled linear guide 420 can accommodate light loads. The collimation assembly 410 may be able to be packaged more conventionally.

Figure 5B:
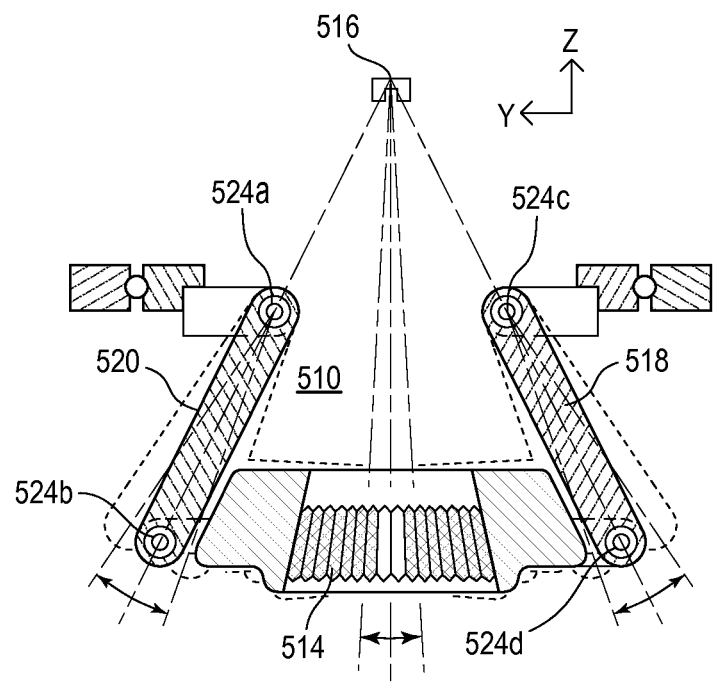
FIG. 5B illustrates a cross-section of an exemplary collimation assembly in accordance some embodiments of the invention.
Figure 5C:
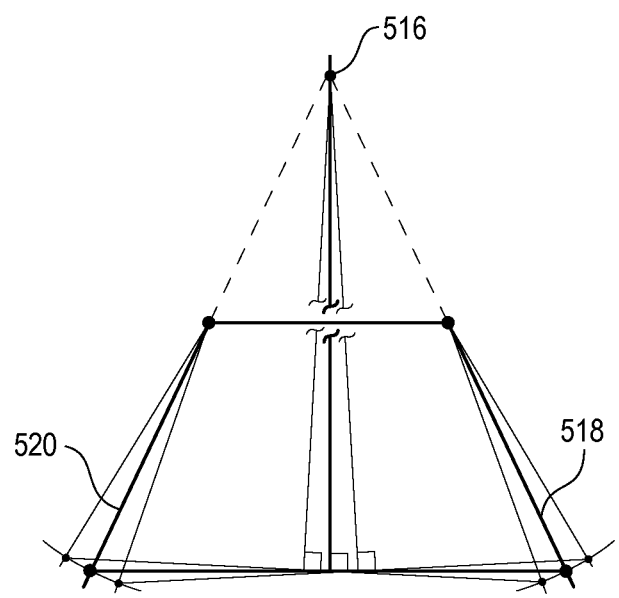
FIG. 5C is a schematic geometry diagram showing transverse motions of the collimation assemblies illustrated in FIGS. 5A and 5B.
Figure 6:
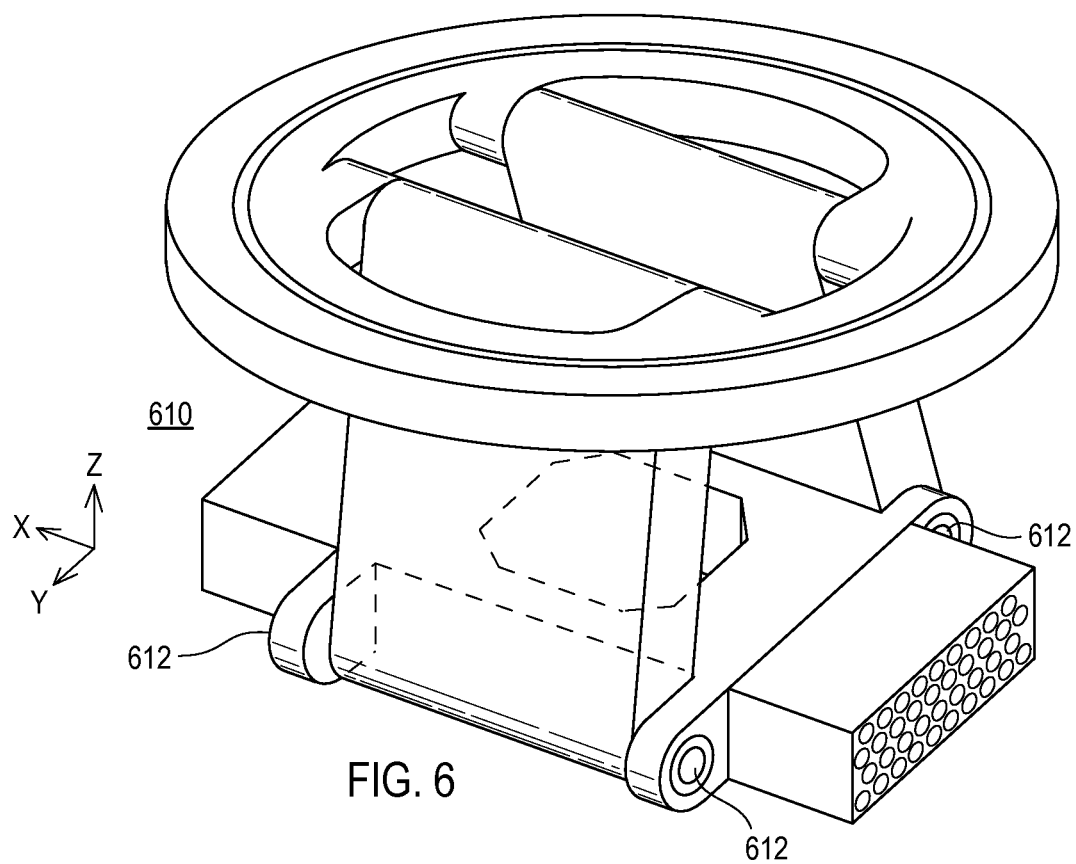
FIG. 6 is an isometric view of the collimation assembly illustrated in FIG. 5B.
Figure 7:
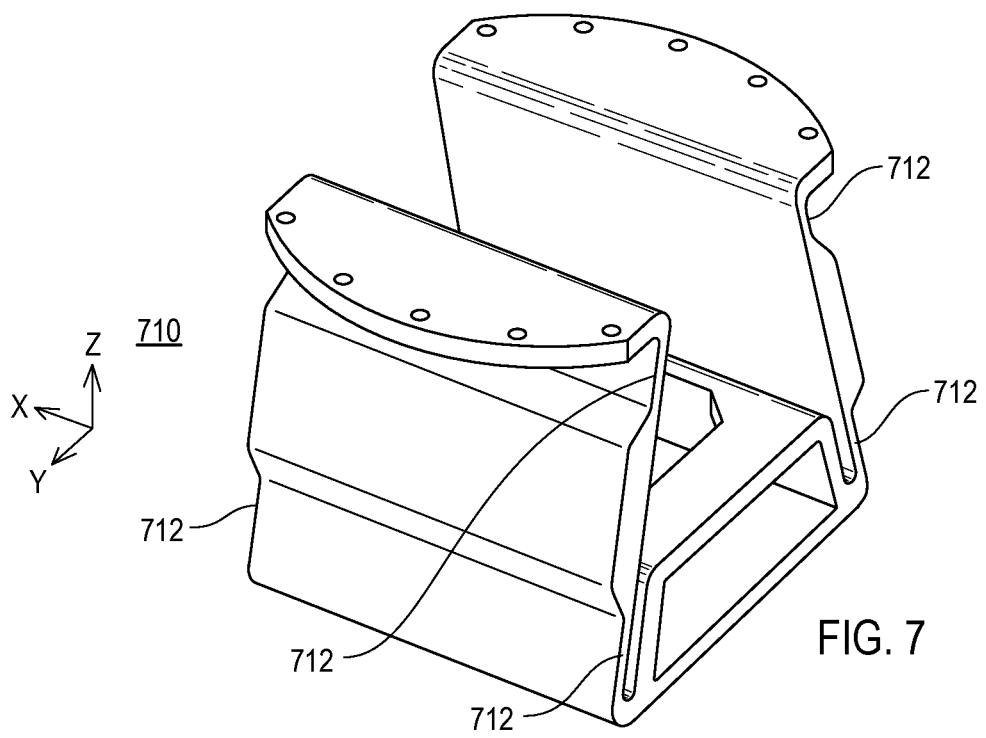
FIG. 7 is an isometric view of the collimation assembly illustrated in FIG. 5A.

FIG. 5A illustrates further alternative construction of a collimation assembly 510, which may include a support body 512 and a plurality of beam blocking leaves 514 arranged substantially focused on a radiation source 516. The collimation assembly 510 applies a geometric principle of four bar linkage to keep the MLC centerline passing approximately through the source 516. In FIG. 5C which illustrates a geometry diagram of transverse motions of the collimation assembly 510, the angled "bars" 518, 520 point toward the radiation source 516 when the assembly is at center position. Since the shorter the angled bars are, the more vertical motion of the support body will occur, which causes undesirable enlargement of the treatment field with offset motion, relatively longer angled bars are preferably used. In the extreme geometry, all angled bars would be joined at the radiation source, and the mechanism would become a rigid triangle body rotating perfectly at the source instead of an approximate four bar linkage. FIG. 5A illustrates an embodiment of angled bars using flexure hinges 522a, 522b, 552c, and 552d as links. FIG. 5B illustrates another embodiment of angled bars using bearing or bushing hinge pairs 524a, 524b, 524c, and 524d as links. The geometry principle of the four bar linkage constructions shown in FIGS. 5A and 5B are the same as illustrated in FIG. 5C. FIG. 6 shows isometric details of a collimation assembly 610 using bearings or bushings 612 in the four bar linkage construction. Some of the eight bearings are not shown. FIG. 7 shows isometric details of a collimation assembly 710 using flexures 712 in the four bar linkage construction. Construction of the flexures may be of few pieces or a single piece. The desired flexure axis behavior may be created from solid pieces by incorporating relatively thinner sections. The behavior of motion degree of freedom of the collimation assemblies 610 and 710 is substantially the same. Flexures may produce light spring forces resisting deflection. Bearing hinge pairs may minimize axial play and deflection through preload and choice of bearing type. When flexure hinges are used, they should be chosen or designed to have sufficient fatigue life and to minimize deflections in all degrees of freedom but that of the hinge axis. The flexure can be in composite construction using thin metals such as spring steel or beryllium copper as shown in FIG. 5A. Flexure can also be made in fewer pieces or a single piece from one material such as aluminum as shown in FIG. 7. The flex characteristics can be tailored by thickness choice using processes such as wire electrical discharge machining (EDM) known in the art. The angled links and the structural links through the collimation assembly and the bearing inner race should be sufficiently rigid in bending, shear, and torsion to provide support at all collimator orientations to gravity.

Figure 8A:
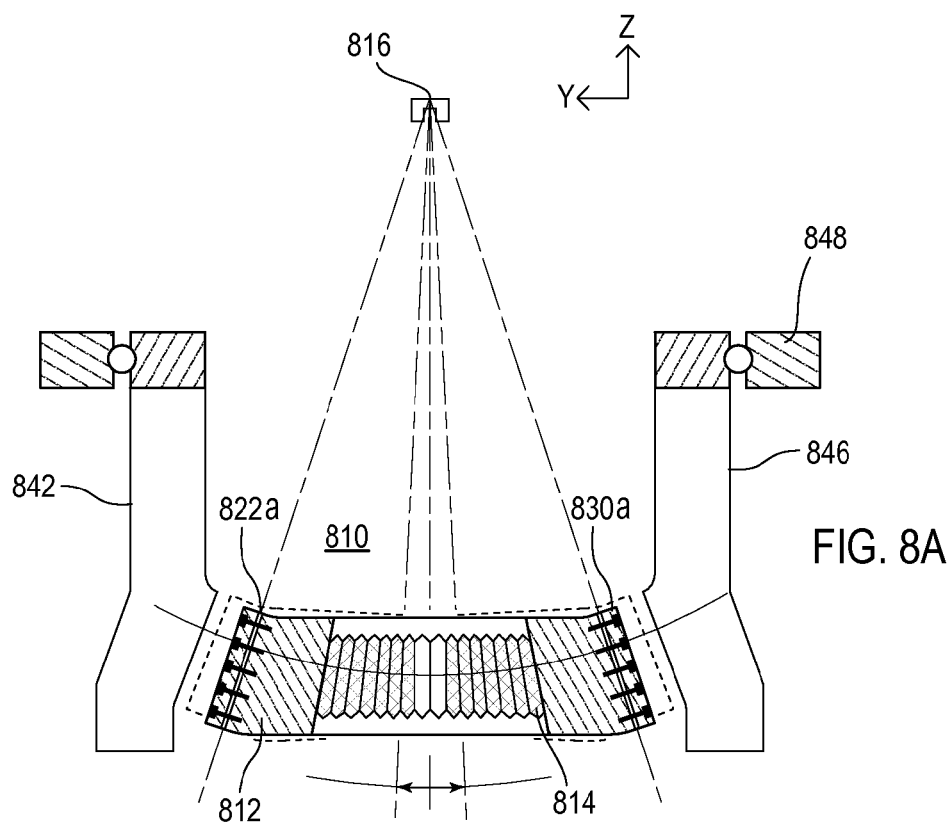
FIG. 8A illustrates a cross-section of an exemplary collimation assembly in accordance with some embodiments of the invention.
Figure 8B:
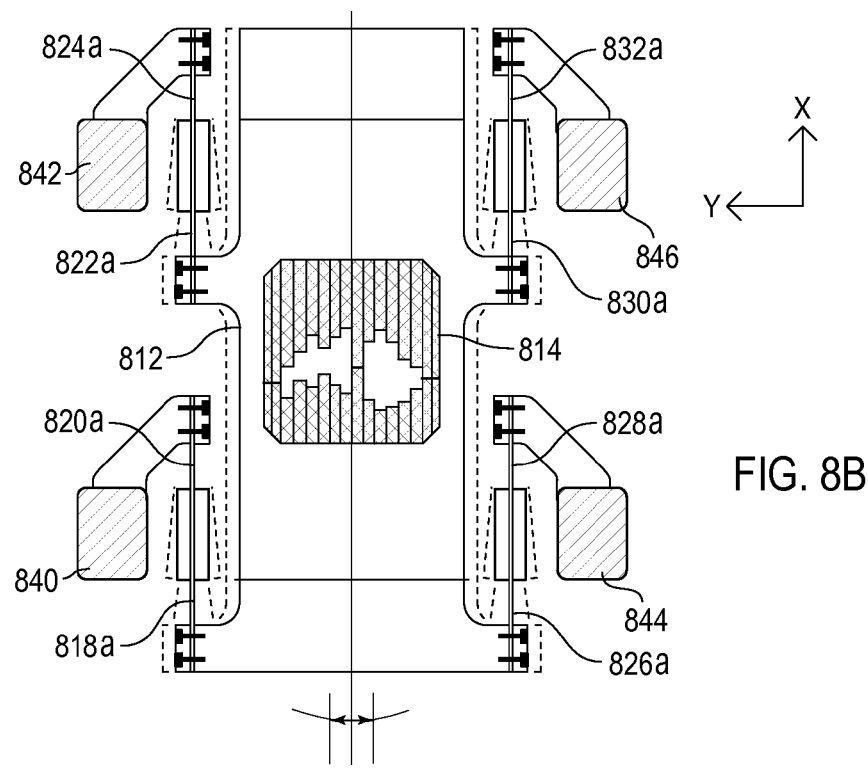
FIG. 8B is a schematic beam's eye plane view of the collimation assembly illustrated in FIG. 8A.
Figure 8C:
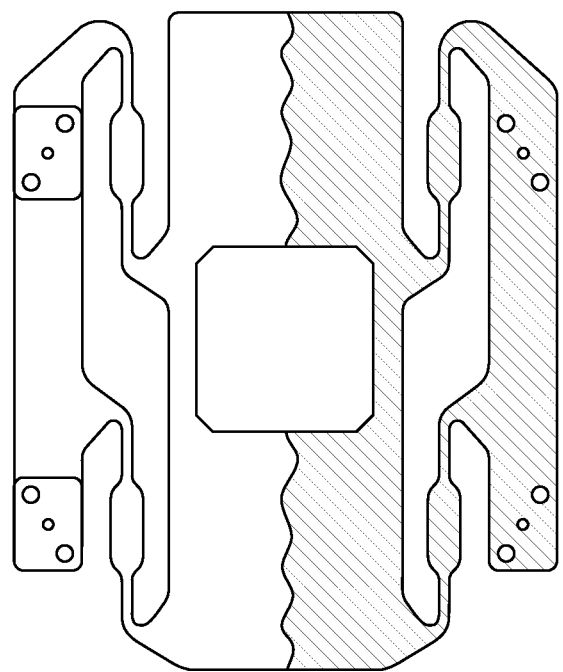
FIG. 8C is a schematic beam's eye cross-section view of an alternative element of a collimation assembly similar to that illustrated in FIG. 8A.
Figure 8D:
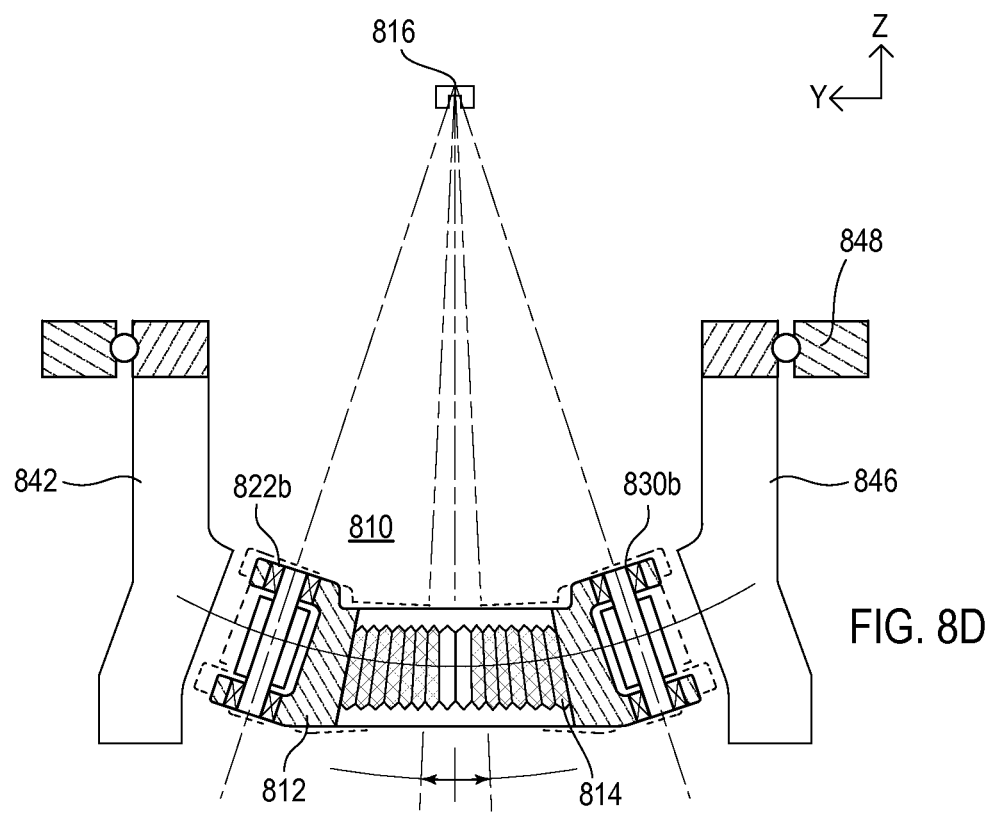
FIG. 8D illustrates a cross-section of an exemplary collimation assembly in accordance with some embodiments of the invention.
Figure 8E:
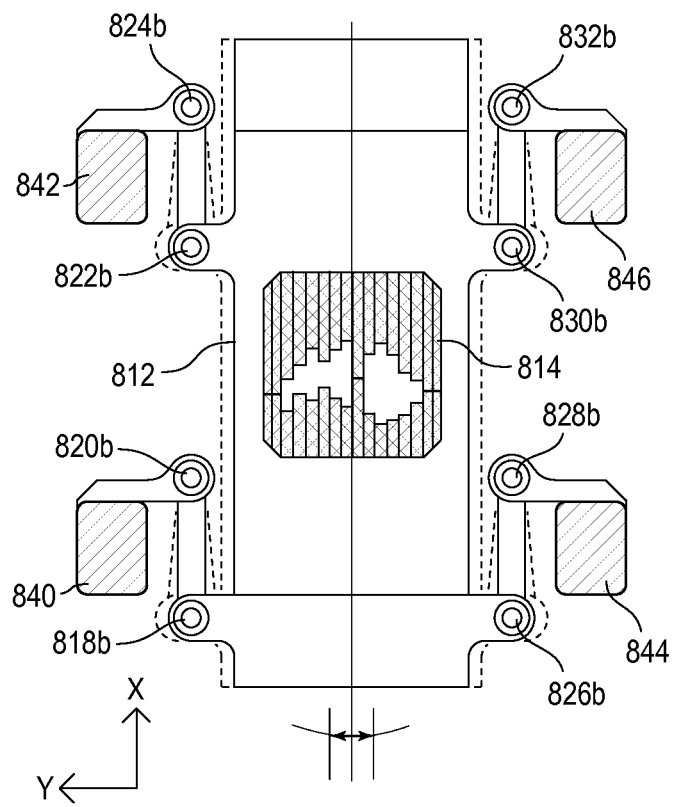
FIG. 8E is a schematic beam'-eye plan view of the collimation assembly illustrated in FIG. 8D.
Figure 8F:
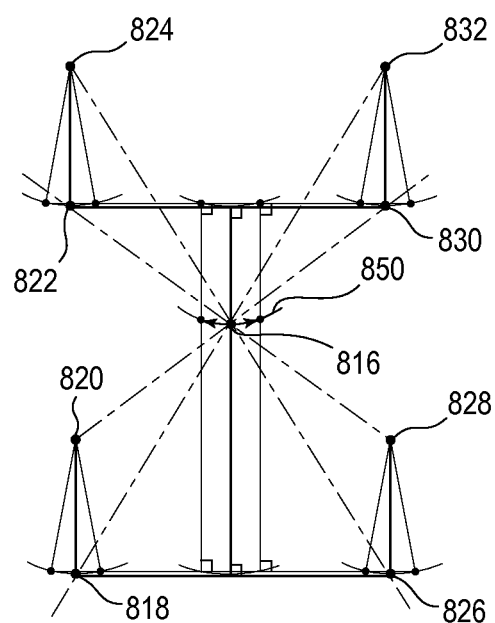
FIG. 8F is a schematic beam's eye view geometry diagram showing transverse motions of the collimation assemblies illustrated in FIGS. 8A and 8D.

FIGS. 8A-8F illustrate alternative constructions of collimation assemblies 810 in accordance with some embodiments. The collimation assemblies 810 includes a support body 812 supporting beam blocking leaves 814 arranged substantially focused on a source 816, and employs a three-dimensional mechanism in moving the support body 812 and beam blocking leaves 814. For illustration purposes, FIG. 8A and FIG. 8B show an embodiment of the angled "bars" using flexure hinges 818a, 820a, 822a, 824a, 826a, 828a, 830a, and 832a. FIG. 8D and FIG. 8E show an embodiment of the angled bars using bearing hinge pairs 818b, 820b, 822b, 824b, 826b, 828b, 830b, and 832b. Either flexure or bearing pair embodiment connects the support body 812 to four structures 840, 842, 844, 846 connected to the rotating race of the collimator bearing 848. Composite flexure construction using thin metal such as spring steel or beryllium copper can be employed as shown in FIGS. 8A and 8B. Flexure made in fewer pieces or a single piece from one material such as aluminum can also be employed as shown in FIG. 8C. The flex characteristics can be tailored by thickness choice using manufacturing processes such as wire EDM processes known in the art. The principles of this embodiment may be made clearer by the beam's-eye view geometry diagram shown in FIG. 8F. All eight hinge axes pass through the radiation source 816. For clarity, the non-perpendicular inclinations of the hinge axes and associated components are not shown in the beam's eye view cross sections FIG. 8B and FIG. 8E. The MLC transverse motion 850 is on the surface of a virtual sphere centered at the radiation source 816. In the beam's-eye view of FIG. 8D, it can be seen that the mechanism moves the MLC not in the pure y direction, but in a slight arc 850, resulting in a very small unwanted movement in the x-direction. The control system can compensate for this using MLC leaf or carriage motion. To improve the rigidity of the mechanism in rotation about the z axis, balanced loads and/or dual synchronized actuator mechanisms may be used. One of the advantages of the mechanism shown in FIGS. 8A-8F is it allows its packaging very local to the MLC, particularly for the one-piece flexure. The embodiments illustrated in FIGS. 8A-8F may also be created with only half of the mechanism depicted. Specific use of only four of the eight hinge axes, for example in FIG. 8B, 822a, 824a, 830a, and 832a, may be sufficient to constrain the motion of the MLC to the desired degree of freedom. The physical features creating the four hinge axes would then have to be relatively taller than in an eight-axis version to achieve the same rigidity. A 4-axis version may reduce cost, but packaging may be more challenging.

Figure 9:
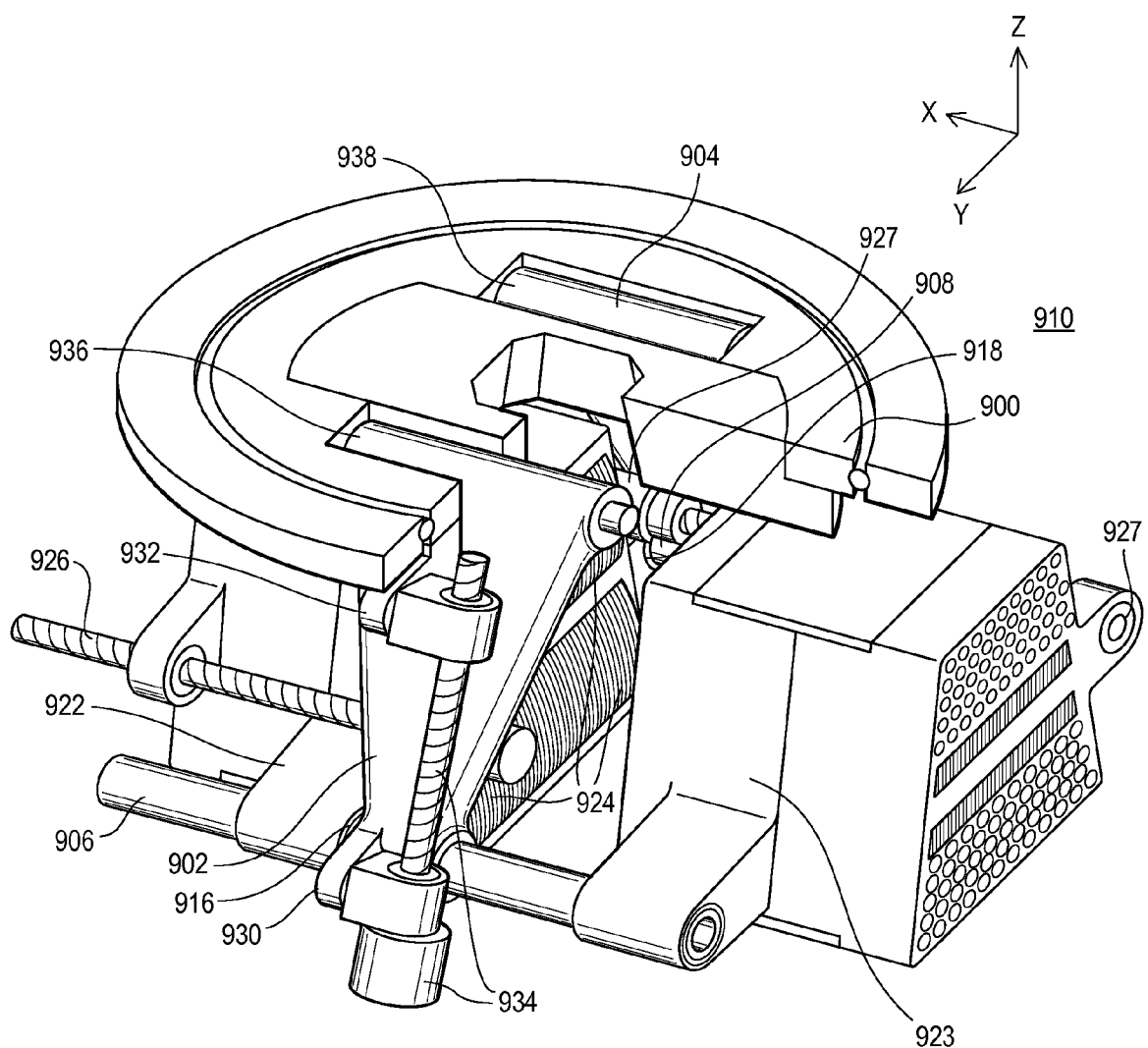
FIG. 9 is a cut-away isometric view of a collimation assembly in accordance with some embodiments of the invention.

FIG. 9 shows a cut-away isometric view of a collimator assembly 910. This embodiment combines the advantages of a multi-level MLC, carriage motion, and small transverse motion. The entire assembly may be attached to the moving race of collimator bearing 900. For transverse motion, this embodiment may use the four bar linkage principle illustrated in FIGS. 5A-5C. Struts 902 and 904 each may support a motion rail 906 and 908, respectively. A carriage 922 may support two sets of MLC leaves 924. The four "bars" of the linkage are 900, 902, 904, and 922. The opposite carriage 923 may act as a redundant "bar" to 922. The four "links" allowing rotation are 916, 918, 936, and 938. Equivalent components duplicated on the opposite side are not identified. Elements 936 and 938 may be bearings or bushings that constrain axial movement. 916 and 918 may be components that allow both rotation and axial movement, such as bushings or cylindrical linear bearings. Use of such components on cylindrical motion rails 906 and 908 as shown allows both the four bar linkage transverse motion and the linear motion of carriages. Other embodiments can also allow both motions, but generally would have to accommodate the linear carriage motion and the linkage rotation separately. For example, the combination of a linear motion stage with a flexure or bearing for the small rotation.

Carriage 922 is shown fully extended and carriage 923 is shown fully retracted, driven respectively by powered actuating mechanisms 926 and 927 of any type described previously such as a motor driving a ballscrew and ball nut assembly. In this embodiment, the mounting points for the ends of the powered actuating mechanisms would have to accommodate a small amount of misalignment caused by the transverse motion. This could be accommodated by incorporating spherical bearings or flexures.

The four bar linkage of this embodiment may be driven by a powered actuating mechanism 934 mounted on rotating trunnion blocks 930 and 932. A small motion of the actuator changes the distance between 930 and 932 and thereby rotates strut 902 relative to collimator bearing 900. This actuates the four bar linkage and provides the proper transverse motion of the MLC.

Figure 10:
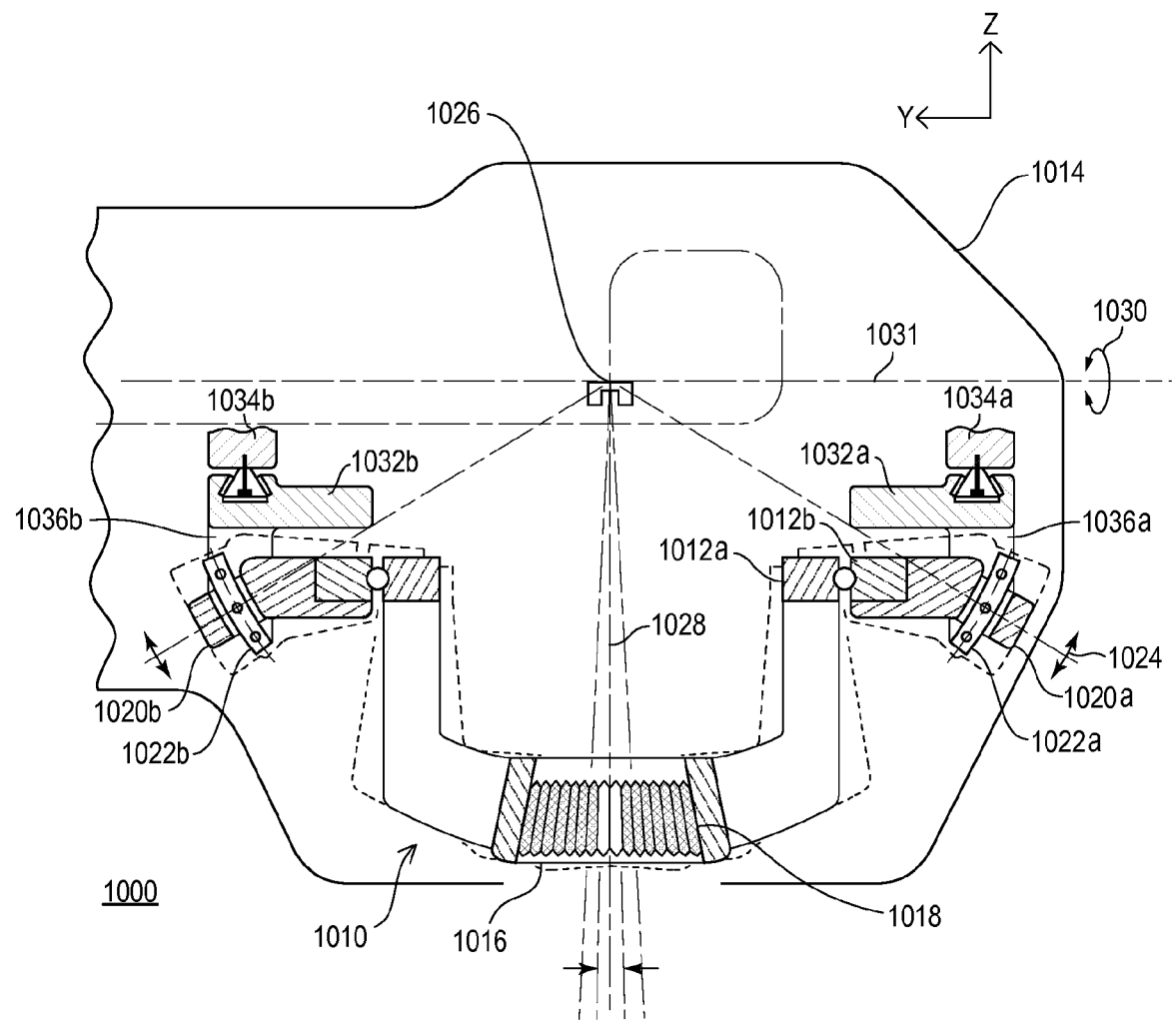
FIG. 10 illustrates a cross-section of an X-ray apparatus including a collimation assembly in accordance some embodiments of the invention.

FIG. 10 illustrates an exemplary X-ray apparatus 1000 including a collimation assembly 1010 of an alternative construction in accordance with some embodiments. The collimation assembly 1010 may be supported by a bearing assembly 1012. The bearing assembly 1012 may include a rotating race 1012a and a non-rotating race 1012b. The collimation assembly 1010 includes a support body 1016 and a plurality of beam blocking leaves 1018 supported by the support body. The support body 1016 may be attached to and supported by the rotating race 1012a of the bearing assembly. The non-rotating race 1012b may be coupled to a first motion assembly including e.g. curved bushings 1020a and 1020b moving on curved bearing rails 1022a and 1022b, which when actuated e.g. by a powered actuating mechanism (not shown) allow the entire collimation assembly 1010 to rotate in a pitch angle 1024 about an axis (out of the paper plane) that is through the source 1026 and perpendicular to the beam axis 1028. A similar second motion assembly may be configured to rotate the entire collimation assembly 1010 in a roll motion 1030 about an axis 1031 that is through the source 1026 and perpendicular to the beam axis 1028. For example, the second motion assembly may include curved bushings 1032a and 1032b moving on curved rails 1034a and 1034b. The rails 1034a and 1034b may be attached to the gantry structure 1014. Support frames 1036a and 1036b may be attached to the bushings 1032a and 1032b and connect to the curved bearing rails 1022a and 1022b.

The apparatus illustrated in FIG. 10 allows a transverse motion of the beam blocking leaves in a structural hierarchy higher than the collimator bearing race. Two or more motion assemblies may be used to provide two or more degrees of freedom and may operate coordinately to provide desired transverse leaf motion. This embodiment allows rotation of the entire collimation assembly relative to the radiation head in two substantially orthogonal axes e.g. pitch and roll, each substantially through the source. Other hierarchical structural arrangements and motion constraining mechanisms such as curved roller bearings, cam followers on curved rails, gimbal arrangement of conventional bearings etc. can be used in this embodiment.

The collimation assemblies of the invention provided with one or more motion degrees of freedom in addition to the MLC leaf and carriage travel can be used in radiotherapy machines to support various dynamic treatments and are particularly useful in tracking tumor motion in radiation therapy. Moving elements of a collimation assembly to track tumor motion allows continuous treatment and fast treatment times. If the changes in the tumor's shape and orientation are negligible as viewed from the radiation source, then the tumor tracking can be simplified by offsetting an instantaneous treatment field location in x, y, and z room coordinates to match the motion of the tumor. Since tumors are generally small compared to their distance to the radiation source, the effect of tumor movement along the beam axis produces only a small change in field size that can usually be ignored. Since the motion of a tumor is typically smaller than about 2 cm, and much of the surrounding tissue is moving with the tumor, angle errors from the source 100 cm distance can also usually be ignored. The challenge then becomes simply to use elements of the collimation system to offset the tumor motion in the other two coordinates of the treatment field orthogonal to the beam axis. These simplifications may allow issues of tumor tracking to be substantially decoupled from treatment planning, simplifying treatment planning and verification.

In planning treatments, if the collimator assembly can be rotated so that the MLC leaf travel direction (e.g. the x direction) matches the direction of tumor movement, then tumor tracking is fairly simple. All of the projected MLC leaf tips in the instantaneous treatment field simply need to be offset by exactly the amount of tumor travel. This can be done with no change to treatment planning by system control commands that modify the planned position of either MLC leaves or MLC carriages based on input from instantaneous sensing of patient breathing or implanted seed movement. Unfortunately, with modern dynamic radiotherapy techniques such as intensity modulated radiation therapy (IMRT) and arc therapy etc., the needs for fluence modulation usually dictate the MLC rotational orientation. Therefore, the MLC leaf travel direction often cannot match the direction of tumor movement in conventional systems. As a result, the planned position of MLC leaves must change in a more complex way in conventional tumor tracking. For any component of tumor movement that is transverse to MLC leaf movement (i.e., in the y direction), individual MLC leaves must respond to the y offset by using their x motion. The individual leaf movement resembles the motion of individual zipper teeth opening and closing. Treatment planning and system control for this action is more complicated than for the y direction offset. The MLC leaf pairs opening and closing the field often must move much faster in the x direction than the tumor movement in the y direction. This may result in undesirable inaccuracies due to lag, and also to beam holds if leaf speed cannot catch up.

This invention provides collimation assemblies with one or more motion degrees of freedom (DOF) in addition to the MLC leaf travel. The additional motion degrees of freedom such as motions transverse to the MLC leaf travel can avoid the problems associated with conventional treatment planning and system control for tumor tracking. For example when in use, a treatment field conforming to the shape and/or size of a tumor in a patient can be defined using a collimation assembly of the invention by positioning the beam blocking leaves relative to a treatment beam. The size and shape information about the tumor can be obtained in a treatment planning session using suitable imaging techniques. The motion of the tumor can also be determined by suitable imaging or sensing implanted seeds, and can be predicted by correlation to the motion of other body parts of the patient such as the patient's abdomen. Movement of the patient's abdomen can be relatively easily measured by tracking external devices such as a respiratory gating block. Rather than zipper-like individual MLC leaf motion as in conventional systems, the construction of the collimation assembly of the invention allows the MLC and thus the treatment field defined by the MLC to move in a direction matching the tumor motion, e.g. in a direction vector with some component generally transverse to the MLC leaf travel direction.

The availability of additional DOF motions and their integration into treatment planning and system control keeps true to radiotherapy community preference to separately handle issues of treatment planning, tumor motion, and patient comfort without complex interdependencies. The collimation assembly of the invention can significantly increase the efficiency in development and quality assurance (QA) of tumor tracking treatment plans. It can also improve the delivery of treatment dose to a patient with less time on a radiotherapy machine.

Figure 11:
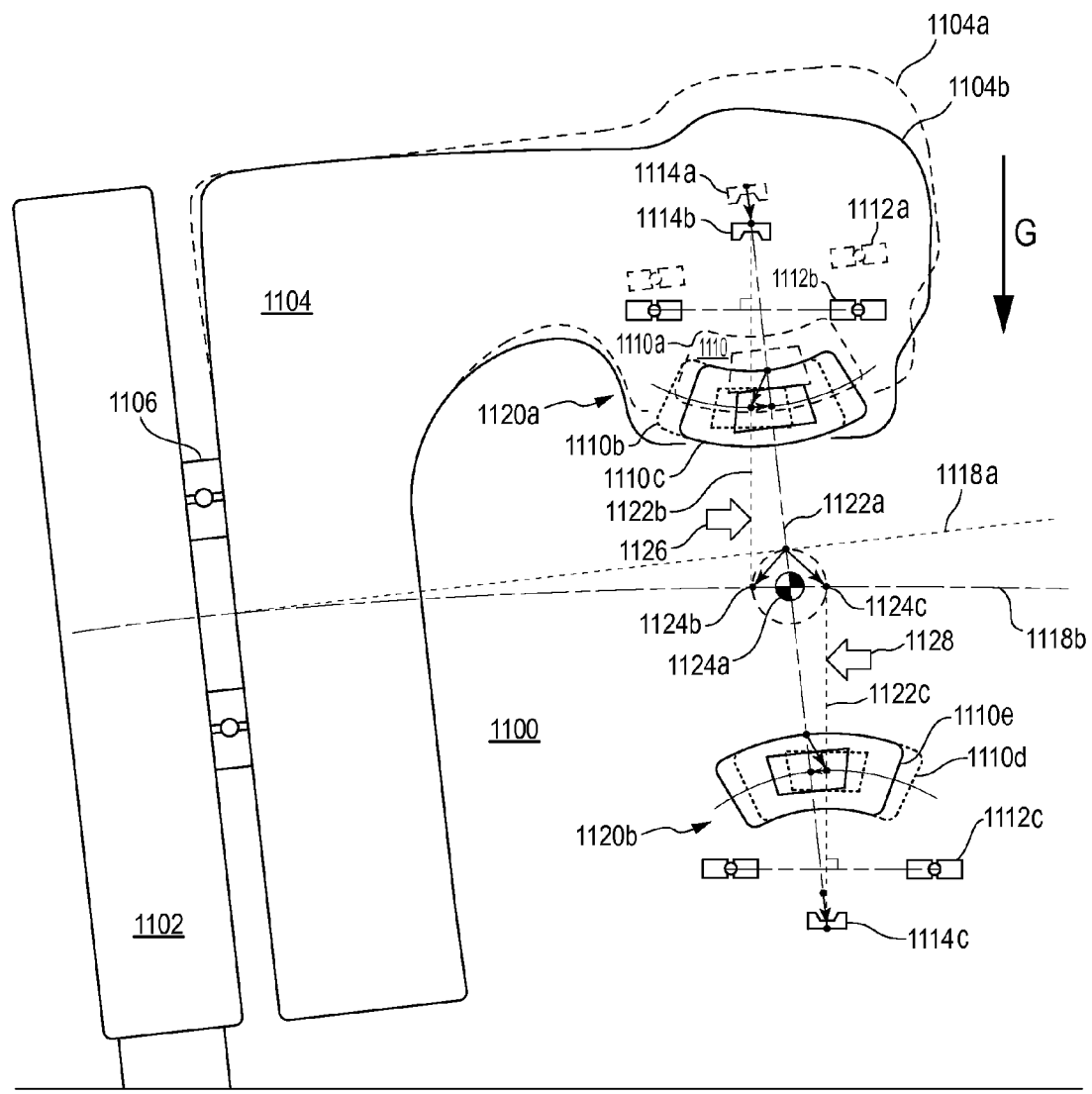
FIG. 11 illustrates a radiation apparatus in accordance with some embodiments of the invention.

The collimation assembly of the invention can also be advantageously used to compensate for beam misalignment in radiation machines. FIG. 11 illustrates an exemplary radiation therapy machine 1100 including a collimation assembly 1110 that is operable to compensate for misalignment in machine motion axes caused e.g. by gravity induced deflection. As shown the radiation machine 1100 may include a stand 1102 which may be anchored on the floor and a gantry 1104 rotatable via a bearing assembly 1106. The collimation assembly 1110 may be supported by a bearing assembly 1112 and include a multileaf collimator configured to selectively block beams from a radiation source 1114. For clarity some elements of the collimation assembly 1110 are omitted in FIG. 11. The collimation assembly 1110 may be provided with one or more motion degrees of freedom in addition to the MLC leaf travel using any of the mechanisms described above.

The gantry 1104 supports heavy parts and may deflect like a cantilever beam, for example as shown from position 1104a to 1104b. This may result in deflection of the gantry rotation axis 1118, deflections of collimation components 1110, or misalignment of beam line or collimator axis 1122. For clarity in illustrating relative locations of machine components, dash lines are used for components at locations as if they were unaffected by gravity. Dot lines are used for the MLC at uncorrected deflected locations. Solid lines are used for the MLC at corrected locations using the method described herein. Dot markers and small arrows are used for direction vectors of the gravity deflections of some components. For instance, in an upright gantry position 1120a, the deflections caused by gravity (G) may bring the radiation source from location 1114a to 1114b, the support bearing from 1112a to 1112b, and the MLC from 1110a to 1110b. Collimator rotation axis may shift from 1122a to 1122b, and gantry rotation axis deflect from 1118a to 1118b. If uncorrected, the collimation rotation axis 1122b and the gantry rotation axis 1118b could intersect at position 1124b, which is away from the isocenter 1124a and closer to the stand 1102. Conversely, in an inverted gantry position 1120b (for clarity only certain parts are shown), the gravity deflections could bring the radiation source to location 1114c, support bearing to location 1112c, and the MLC to location 1110d. If uncorrected the gantry rotation axis 1118b and collimator rotation axis 1122c could intersect at position 1124c, which is away from the isocenter 1124a and farther from to the stand 1102. Isocenter error represented by the dot line circle containing these intersections 1124b, 1124c could be large and clinically significant.

The motion degree or degrees of freedom of the collimation assembly in addition to the MLC leaf travel can be advantageously used to compensate for many unwanted effects of deflections and make the isocenter error smaller. The compensation method may move the MLC shaped aperture so that it projects through the same compensated isocenter 1124a regardless of deflections. Stubby arrows 1126 and 1128 show the direction of MLC aperture compensation movement. The MLC may be moved in an arc as shown. It will be appreciated that the MLC movement can be in any trajectory and in any direction, same as or different from the MLC leaf travel direction as described above in conjunction with other embodiments. If the collimator rotation were momentarily about 90 degree different from that as shown, then the motion of MLC carriages or leaves could also be used to compensate for the deflection effects. In FIG. 11, the corrected MLC location is shown at 1110c (upright gantry position) and 1110e (inverted gantry position). The collimator rotation axes 1122b and 1122c are not corrected and remain at the dot line locations.

It will be appreciated that the collimation assembly provided with one or more degrees of freedom in addition to MLC leaf travel can be used to compensate for beam misalignment caused by any errors including but not limited to those due to imperfections of machining and assembly, gravity deflections of machine components while the gantry is rotating, and so on. Imperfections of machining and assembly may cause the gantry rotation axis and the collimator rotation axis to not intersect ("head skew") even if there were zero gravity influence. Gravity deflections of the structures while the gantry is rotating may cause the collimator axis to be not always perfectly intersecting some point in fixed space (the isocenter). In addition, misalignment could be within collimator itself. Shift of machine components may occur due to any reasons not just one of gravity. These and other errors may cause beam misalignment with respect to the isocenter, which may be clinically significant especially for small target volumes. The misalignment can be measured using methods well known to the ordinary skill in the art. For instance, the measurement of misalignment may involve projected X-ray images of the beam aperture at various orientations. The misalignment data may be provided to a control system, which can translate the information into compensation factors for various motion axes, including those as described above providing the collimation assembly with one or more degrees of freedom.

Those skilled in the art will appreciate that various other modifications may be made within the spirit and scope of the invention. All these or other variations and modifications are contemplated by the inventors and within the scope of the invention.

What is claimed is:

1. A collimation assembly for selectively blocking radiation beams having a beam axis comprising a multileaf collimator and a motion assembly, wherein
the multileaf collimator comprises a support body and a plurality of pairs of beam blocking leaves supported by the support body, leaves of each pair being longitudinally movable in a first direction; and
the motion assembly comprises an actuator and a guide assembly operable to move the support body thereby allowing the plurality of pairs of beam blocking leaves to move in a second direction generally transverse to the first direction and the beam axis.

2. The collimation assembly of claim 1 wherein the plurality of pairs of leaves are arranged to substantially focus on a source, and the motion assembly is operable to move the support body thereby allowing the plurality of pairs of leaves to move in the second direction substantially in an arc trajectory substantially centered on the source.

3. The collimation assembly of claim 1 wherein the collimation assembly is movable generally transverse to the beam axis.

4. The collimation assembly of claim 1 further comprising a second motion assembly operable to move the support body thereby allowing the plurality of pairs of leaves to move in a third direction generally parallel to the first direction.

5. The collimation assembly of claim 4 wherein the second motion assembly is operable to allow the plurality of pairs of leaves to move in an arc trajectory substantially centered on a source.

6. The collimation assembly of claim 1 wherein the support body comprises one or more movable carriages operable to move the plurality of leaves in a third direction substantially parallel to the first direction.

7. A radiation apparatus comprising a radiation source operable to generate a beam having a beam axis and a collimation assembly operable to selectively block the beam, said collimation assembly comprises a multileaf collimator and a motion assembly, wherein
the multileaf collimator comprises a support body and a plurality of pairs of beam blocking leaves supported by the support body, leaves of each pair being longitudinally movable relative each other; and
the motion assembly comprises an actuator and a guide assembly operable to move the support body relative to the radiation source thereby allowing the beam blocking leaves to rotate about an axis that is angled relative to the beam axis.

8. The radiation apparatus of claim 7 wherein the plurality of pairs of leaves are longitudinally movable in a first direction, and the motion assembly is operable to move the support body in a second direction generally transverse to the first direction.

9. The radiation apparatus of claim 7 wherein the plurality of pairs of leaves are longitudinally movable in a first direction, and the motion assembly is operable to move the support body in a second direction generally parallel to the first direction.

10. The radiation apparatus of claim 7 wherein the plurality of pairs of leaves are longitudinally movable in a first direction, and the motion assembly is operable to move the support body in a direction generally transverse to the first direction and in a direction generally parallel to the first direction.

11. The radiation apparatus of claim 7 wherein the motion assembly is operable to rotate the support body about the axis that is substantially through the source and substantially perpendicular to the beam axis.

12. A radiation apparatus comprising:
a radiation source operable to generate a beam having an axis;
a collimation assembly operable to selectively block the beam, said collimation assembly comprising a multileaf collimator which comprises a support body and a plurality of pairs of beam blocking leaves supported by the support body, leaves of each pair being longitudinally movable relative each other;
a bearing assembly supporting the collimation assembly; and
a motion assembly operable to move the bearing assembly relative to the radiation source thereby allowing the collimation assembly to rotate about an axis that is angled relative to the beam axis.

13. The radiation apparatus of claim 12 wherein the motion assembly is operable to rotate the bearing assembly in two or more degrees of freedom thereby allowing the collimation assembly to rotate in two or more degrees of freedom.

14. A radiation apparatus comprising a radiation source and a collimation assembly which comprises a multileaf collimator and a motion assembly, wherein
the multileaf collimator comprises a support body and a plurality of pairs of beam blocking leaves supported by the support body, leaves of each pair being longitudinally movable relative each other in a first direction; and the motion assembly comprises an actuator and a guide assembly operable to move the support body relative to the radiation source thereby allowing the beam blocking leaves to move in a second direction substantially in an arc that is centered substantially at the radiation source.

15. The radiation apparatus of claim 14 wherein the motion assembly comprises a four bar linkage mechanism where one bar comprises the support body.

16. The radiation apparatus of claim 14 wherein the motion assembly comprises an eight-axis mechanism connected to the support body, wherein the eight axes are substantially focused on the source and the motion of the support body is substantially on the surface of a sphere that is centered substantially at the source.

17. The radiation apparatus of claim 14 wherein the motion assembly comprises a four-axis mechanism connected to the support body, wherein the four axes are substantially focused on the source and the motion of the support body is substantially on the surface of a sphere that is centered substantially at the source.

18. A radiation apparatus comprising a radiation source and a collimation assembly, said collimation assembly comprises:
the multileaf collimator comprises a support body and a plurality of pairs of beam blocking leaves supported by the support body in two or more levels in a beam direction, leaves of each pair being longitudinally movable relative each other;
a first motion assembly operable to move the support body in a first direction; and
a second motion assembly operable to move the support body in a second direction different from the first direction.

19. The radiation apparatus of claim 18 wherein said second motion assembly comprises a four bar linkage mechanism where one bar comprises the support body.

20. A radiation method comprising:
providing a radiation beam from a source to a target in a subject;
defining a treatment field substantially conforming to the shape of the target using a multileaf collimator assembly comprising a support body and a plurality of beam blocking leaves supported by the support body, the plurality of beam blocking leaves being movable in a first direction, the treatment field being defined at least by positioning the plurality of beam blocking leaves relative to the beam; and
moving the defined treatment field in response to a motion of the target by moving the support body relative to the source in a second direction that is different from the first direction of the beam blocking leaves.

21. The radiation method of claim 20 wherein the defining step comprises moving at least a portion of the plurality of leaves longitudinally in the first direction, and the moving step comprises moving the support body in the second direction generally transverse to the first direction.

22. The radiation method of claim 20 wherein the moving step comprises moving the support body in an arc trajectory substantially centered on the radiation source.

23. A method of compensating for a beam misalignment in a radiation machine which comprises a radiation source and a multileaf collimator including a plurality of pairs of beam blocking leaves longitudinally movable in a first direction,
the method comprising the step of moving the plurality of pairs of leaves in a second direction generally transverse to the first direction and an axis of a beam from the radiation source.

24. The method of claim 23 wherein the moving step comprises moving the plurality of pairs of leaves generally in an arc.

* * * * *